(12) United States Patent
Jothimuthu et al.

(10) Patent No.: US 10,527,577 B2
(45) Date of Patent: Jan. 7, 2020

(54) NANOGRID ELECTROCHEMICAL SENSOR FOR DETECTION OF BIOCHEMICAL SPECIES BY ELECTROCHEMICAL IMPEDANCE SPECTROSCOPY

(71) Applicants: The Board of Trustees of the Leland Stanford Junior University, Palo Alto, CA (US); The United States of America as represented by the Department of Veteran Affairs (Washington DC), Washington, DC (US)

(72) Inventors: Preetha Jothimuthu, Santa Clara, CA (US); Mohammed Inayathullah Nazir Ahmed, Santa Clara, CA (US); Wen A. Tian, Redwood City, CA (US); Jayakumar Rajadas, Cupertino, CA (US); Mark Nicolls, Palo Alto, CA (US); JooChuan Ang, Berkeley, CA (US)

(73) Assignees: The Board of Trustees of the Leland Stanford Junior University, Stanford, CA (US); The United States of America as represented by the Department of Veteran Affairs (Washington DC), Washington, DC (US)

( * ) Notice: Subject to any disclaimer, the term of this patent is extended or adjusted under 35 U.S.C. 154(b) by 0 days.

(21) Appl. No.: 15/653,336

(22) Filed: Jul. 18, 2017

(65) Prior Publication Data
US 2018/0017518 A1    Jan. 18, 2018

Related U.S. Application Data

(60) Provisional application No. 62/363,727, filed on Jul. 18, 2016.

(51) Int. Cl.
  *C25D 13/20*  (2006.01)
  *C25D 5/02*   (2006.01)
  (Continued)

(52) U.S. Cl.
  CPC ............ *G01N 27/3278* (2013.01); *B01L 3/50* (2013.01); *C23C 18/1824* (2013.01);
  (Continued)

(58) Field of Classification Search
  CPC .................................. C25D 13/02; C25D 5/48
  See application file for complete search history.

(56) References Cited

U.S. PATENT DOCUMENTS

| | | | |
|---|---|---|---|
| 7,510,638 B2 * | 3/2009 | Herman | B82Y 30/00 204/490 |
| 8,425,745 B2 | 4/2013 | Briman et al. | |

(Continued)

OTHER PUBLICATIONS

Pitt et al, "Albumin adsorption on alkyl chain derivatized polyurethanes. II. The effect of alkyl chain length" Biomaterials (1988), 9(1), 36-46. Abstract provided. (Year: 1988).*

(Continued)

*Primary Examiner* — Brian W Cohen
(74) *Attorney, Agent, or Firm* — Lumen Patent Firm

(57) ABSTRACT

Improved electrochemical impedance spectroscopy assays are provided by electrodepositing metallic nanoparticles onto the working electrode for electrochemical impedance spectroscopy. The metallic nanoparticles provide improved assay sensitivity. Electrodeposition of the metallic nanoparticles firmly affixes them to the working electrode, thereby making it easier to clean the working electrode from one assay to the next assay without undesirably removing the metallic nanoparticles.

4 Claims, 8 Drawing Sheets

(51) Int. Cl.

| | |
|---|---|
| *C25D 13/02* | (2006.01) |
| *G01N 27/327* | (2006.01) |
| *G01N 27/414* | (2006.01) |
| *G01N 33/53* | (2006.01) |
| *B01L 3/00* | (2006.01) |
| *C23C 18/18* | (2006.01) |
| *C23C 18/31* | (2006.01) |
| *G01N 33/543* | (2006.01) |

(52) U.S. Cl.
CPC .............. *C23C 18/31* (2013.01); *C25D 13/02* (2013.01); *C25D 13/20* (2013.01); *G01N 27/4145* (2013.01); *G01N 27/4146* (2013.01); *G01N 33/53* (2013.01); *G01N 33/5438* (2013.01); *C25D 5/02* (2013.01)

(56) References Cited

U.S. PATENT DOCUMENTS

2012/0037515 A1    2/2012  Solanki
2015/0369806 A1*  12/2015  Wang .............. G01N 33/56983
                                                      435/5

OTHER PUBLICATIONS

Utgenannt et al., "Fast Assembly of Gold Nanoparticles in Large-Area 2D Nanogrids Using a One-Step, Near-Infrared Radiation-Assisted Evaporation Process", 2016, ACS Nano v10, pp. 2232-2242.

* cited by examiner

NANOGRID ELECTROCHEMICAL SENSOR FOR DETECTION OF BIOCHEMICAL SPECIES BY ELECTROCHEMICAL IMPEDANCE SPECTROSCOPY

CROSS REFERENCE TO RELATED APPLICATIONS

This application claims the benefit of U.S. provisional patent application 62/363,727, filed on Jul. 18, 2016, and hereby incorporated by reference in its entirety.

GOVERNMENT SPONSORSHIP

This invention was made with Government support under contract HL014985 awarded by the National Institutes of Health. The Government has certain rights in the invention.

FIELD OF THE INVENTION

This invention relates to assays using electrochemical impedance spectroscopy.

BACKGROUND

Assays are often used for chemical or biochemical analysis. Typically a sensor is coated with an immobilized receptor species (e.g., an antibody), and detection of target species (e.g., antigens) corresponding to the immobilized receptor is performed by sensing bound target-receptor complexes with the sensor. A wide variety of sensor and sensing technologies have been employed in such applications. One such approach is electrochemical impedance spectroscopy, where the bound target-receptor complexes alter an electrical impedance of the sensor. Characterization of this impedance change (typically vs. applied electrical frequency) provides the desired assay signal. In some cases, the sensitivity of an electrochemical impedance spectroscopy is lower than desired. Accordingly, it would be an advance in the art to provide improved electrochemical impedance spectroscopy for chemical and/or biochemical assays.

SUMMARY

In this work, electrochemical impedance spectroscopy is used as the sensing methodology. Furthermore, the sensor includes metallic nanoparticles conjugated to the antibody being used for the assay. Here nanoparticles are defined as particles with any shape having a largest dimension of less than 1 micron. These nanoparticles are bound to the working electrode for electrochemical impedance spectroscopy using an electrochemical deposition process. Here electrochemical deposition of metallic nanoparticles is defined as either 1) the deposition of metallic nanoparticles in solution (e.g. a colloidal suspension) on an electrode by application of an electric field, or 2) the direct formation of metallic nanoparticles on the working electrode from metal ions in solution by application of an electric field. The working electrode is preferably configured as a nano-grid having apertures in it on the order of 100 nm in size (prior to deposition of the nanoparticles).

This configuration provides significant advantages. 1) The resulting electrode structure advantageously provides greater control of electrode configuration than can be obtained with conventional nano-porous electrodes. 2) The metallic nanoparticles increase the sensitivity of the electrochemical impedance spectroscopy assay. 3) Deposition of the metallic nanoparticles on the working electrode via electrodeposition (as opposed to other methods such as sputtering) provides improved adhesion of the metallic nanoparticles to the working electrode. Such improved adhesion is helpful when cleaning the working electrode to prepare for an assay, because the goal of such cleaning is to remove receptors and bound target-receptor complexes while leaving the metallic nanoparticles affixed to the working electrode. The more firmly attached the metallic nanoparticles are to the working electrode, the easier such cleaning will be to perform. 4) This approach is expected to be faster and have lower cost than current methods such as ELISA (enzyme-linked immunosorbent assay) and mass spectrometry.

DETAILED DESCRIPTION

Introduction

In the following description, an exemplary design of an assay for the biological species LTB4 (leukotriene B4) according to the above described principles is considered. However, the present approach is applicable for assays of any chemical species, both biological species and non-biological species.

Research has shown that in the condition of pulmonary hypertension, macrophages produce high levels of leukotriene A4 hydrolase (LTA4H) in response to inflammation and this synthesized leukotriene B4 (LTB4). It was found that by blocking LTB4, the endothelial injury was prevented and the pulmonary hypertension was reversed. The detection of LTB4 can be used for diagnosis of pulmonary hypertension and the hypothesis of detection is based on antigen-antibody binding which would capture the LTB4 onto the sensor surface. Here the method of detection is by electrochemical impedance spectroscopy which would detect the change in impedance upon binding of LTB4. LTB4 detection (more generally, detection of any target species) can be done in samples including but not limited to: tissue biopsy samples, plasma, whole blood, serum, sweat, bronchoalveolar lavage fluids and colon fluids.

The sensor's preferred design of a nanogrid along with electrochemical impedance spectroscopy will improve detection relative to other approaches such as self assembled monolayer sensor surfaces, nanowires, plasmonic substrate chips and nanoporous substrates for detection of biomolecules by methods such as optical, mechanical and electrical sensing shown previously in literature. In one design, the grid lines have a dimensional range of 100 nm (after the electrodeposition of the metal nanoparticle-antibody conjugate, the spacing between the grid lines will decrease much further simulating a nanoporous substrate). Alternatively, the dimension of the grid lines can range from 50 nm to 500 nm. Platinum metal is used for the sensor patterning in this demonstration but other similar metals (e.g., gold, titanium, copper, or aluminum) can also be used. Additionally, the illustrated shape of the nanogrid can be modified to suit the purpose to achieve an ultrasensitive detection.

Sensor Design and Detection:

Electrochemical impedance spectroscopy is an important method to detect changes that happen from binding of biomolecules on the transducer surface. In this method, however, an amplification step is needed if the molecule that being detected is too small. In this research work, the molecule of interest, LTB4, is a small molecule in size and hence an amplification step is included and the phenomenon of binding is described as follows. Metal nanoparticles are conjugated with the LTB4 antibody. This conjugate is then selectively coated on the nanogrid by means of electrodeposition.

Figure 1:
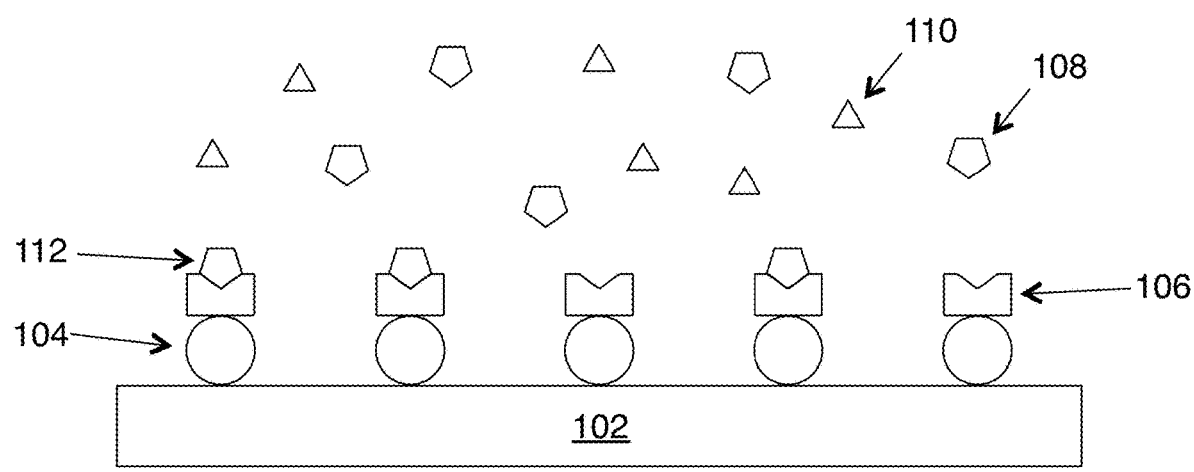
FIG. 1 schematically shows an electrochemical impedance assay according to an embodiment of the invention.

FIG. 1 schematically shows the resulting assay. Here 102 is the working electrode, 104 are the metallic nanoparticles, 106 are the receptors (e.g., LTB4 antibody) conjugated to the metallic nanoparticles, LTB4 in solution is referenced at 108 and other species are referenced as 110. Species-selective bound target-receptor complexes are shown as bound LTB4 112 in receptors 106.

This novel means of immobilization of the antibody-metal nanoparticle conjugate will result in a strong adherence to the working electrode surface. This is because of the establishment of chemical bonding resulting from the exchange of electrons during electrodeposition and the modification of the metal nanoparticles of the conjugate. Moreover, the electrodeposition and resulting immobilization will happen on all exposed areas of the nanogrid lines which is designed in a manner conducive to the electrodeposition on top of the grid lines and the sides of the grid lines. This will narrow the spacing between the grid lines further and appear similar to the surface area of a porous substrate but in a much more controlled manner. The unbound conjugates will be washed off and the impedance before the assay with the LTB4 will be recorded.

Figure 2:
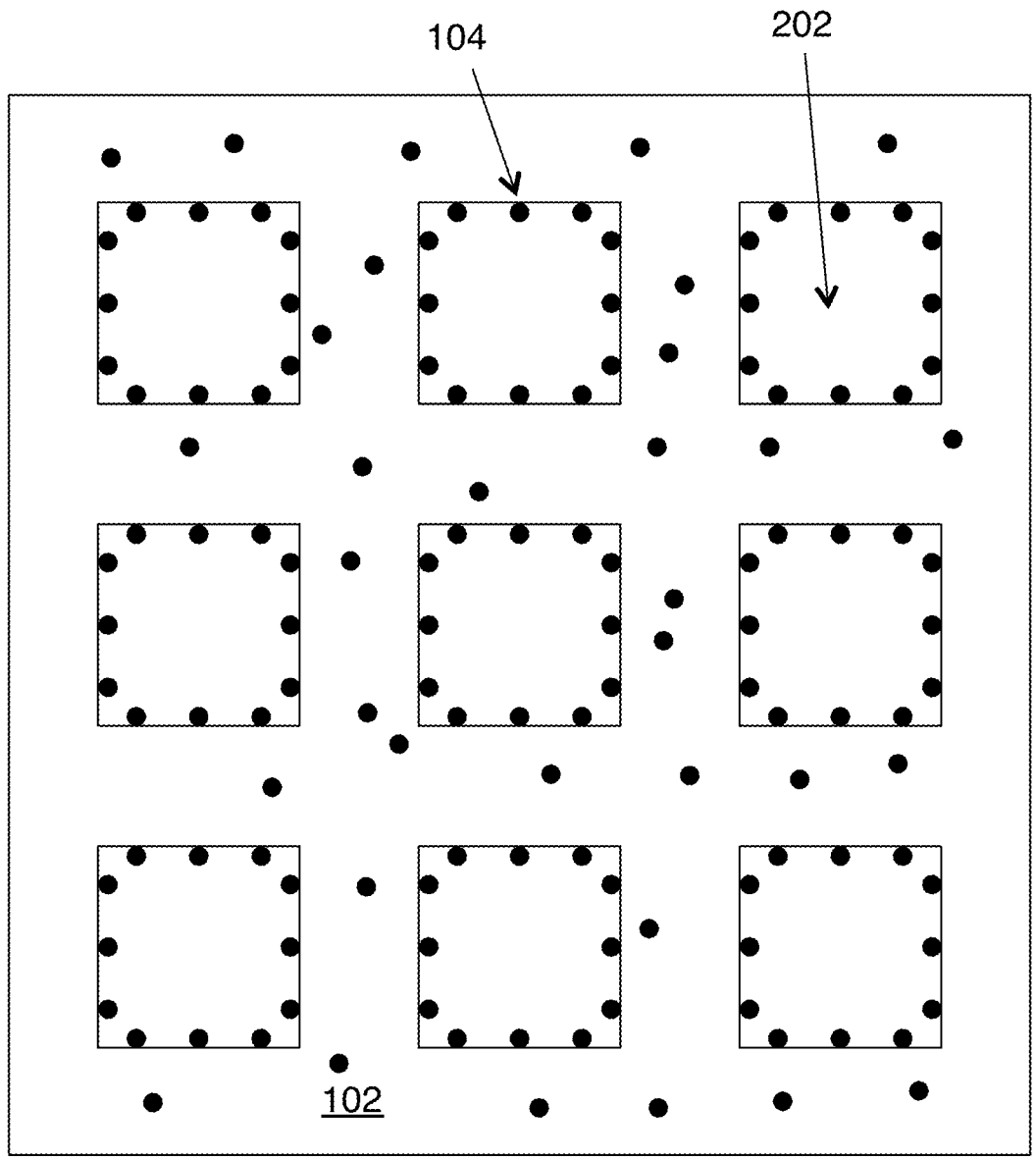
FIG. 2 shows a preferred electrode configuration for performing an electrochemical impedance assay according to an embodiment of the invention.

FIG. 2 shows an example of this electrode arrangement. Here working electrode 102 is configured as a grid having apertures 202. Metallic nanoparticles 104 are deposited on side walls of apertures 202 as shown, and on top of working electrode 102, also as shown.

Figure 2A:
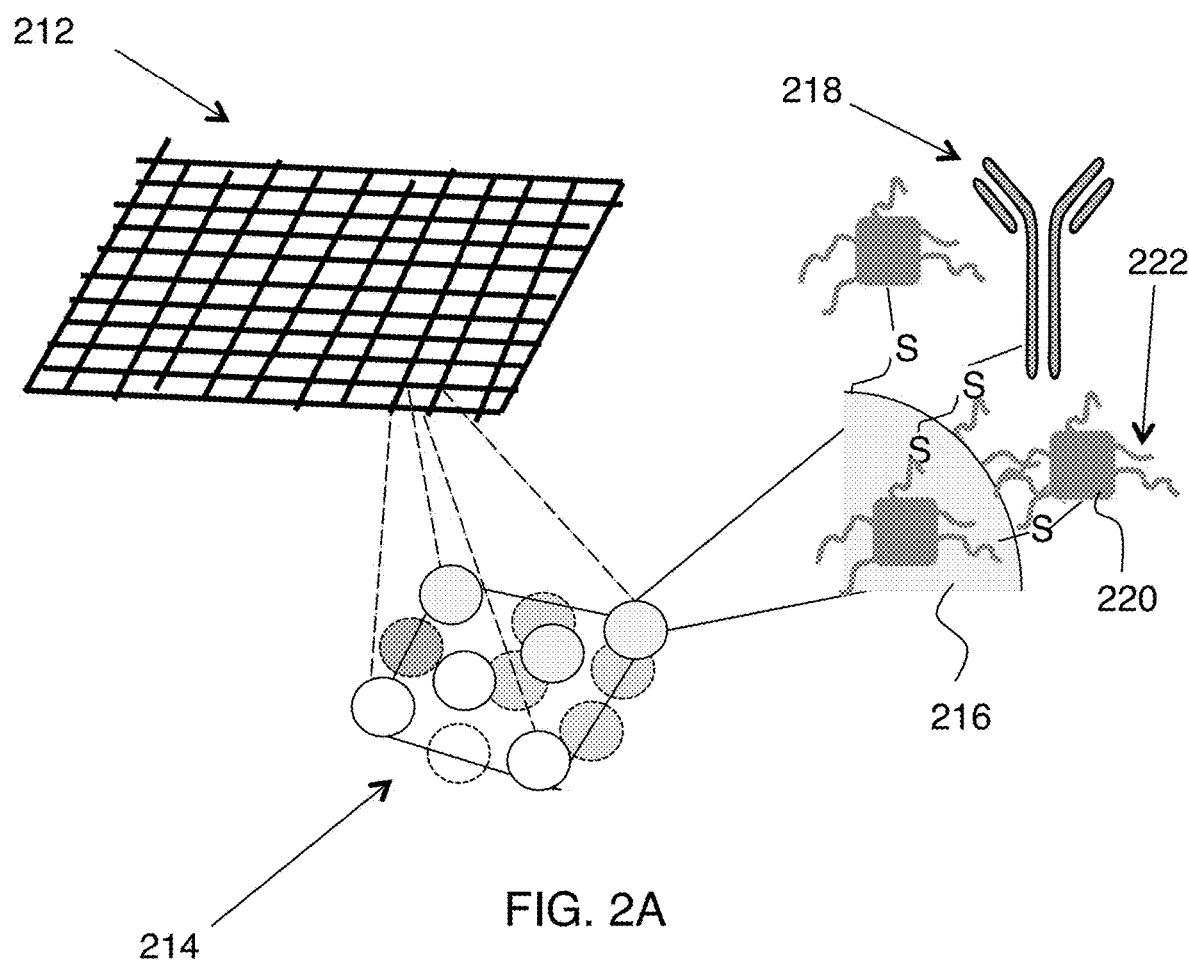
FIG. 2A shows an embodiment of the invention having albumin conjugated to the metallic nanoparticles.

FIG. 2A shows an example of a nanogrid 212 with metallic nanoparticles 216 conjugated with LTB4 sensing antibody 218 and conjugated hydrocarbons 222 bound to immobilized serum albumin 220. Here 214 shows an enlarged view of a nanogrid aperture having multiple nanoparticles in it. In this example, the gold nanoparticles can be bi-functionalized with amine and sulfhydryl groups. The nanogrid can be coated with a mono-protected dithiol spacer (S on FIG. 2A), such as 2,2'-(ethylenedioxy)diethanethiol with one sulfhydryl group protected with methoxytrityl [(4-methoxyphenyl)diphenylmethyl] (MMT). Next, the MMT protecting group can be removed by 1% trifluoroacetic acid in dimethylformamide. Antibody functionalized with maleimide can be chemically conjugated to the metallic nanoparticle surface by reacting with the sulfhydryl groups. Unconjugated sulfhydryl groups will be sequestered by N-acetyl cysteine. This is an important step to prevent serum albumin from covalently binding to the free sulfhydryl groups. Next, the amine groups can be modified with alkyl chains between 14 to 18 carbons long. Serum albumin (human or bovine, defatted) can be bound to the alkyl chains, and thereby physically adsorbed onto the nanoparticle and nanogrid, providing a protein environment around the antibody for structural and activity stabilization. Saturated fatty acids between 14 and 18 carbons long can be added to the substrate to saturate the hydrophobic binding sites within serum albumin.

The main advantages of this novel method of immobilization are that of stronger and more reliable immobilization of the conjugate compared to other existing methods such as self assembled monolayer, layer by layer techniques, entrapment in sol-gel matrix or other optical method of detection where the antibodies are in suspension in the solution. By means of this method of immobilization, it is also easier to clean the electrode of all antibodies and antigen by means of an electrochemical cleaning step so that reliability and accuracy for the subsequent measurements are increased. Moreover, the immobilization can be done by first conjugating the receptors to metal nanoparticles or alternatively by first electrodepositing the metal nanoparticles and then conjugating the receptors to the electrodeposited layer. The assay of the target to the receptor will cause change in the impedance spectroscopy measurements before and after binding of the target to its receptor. The role of the metal nanoparticles is dual: for signal amplification and for selectively coating the nanogrid as shown in FIGS. 1 and 2.

Figure 3:
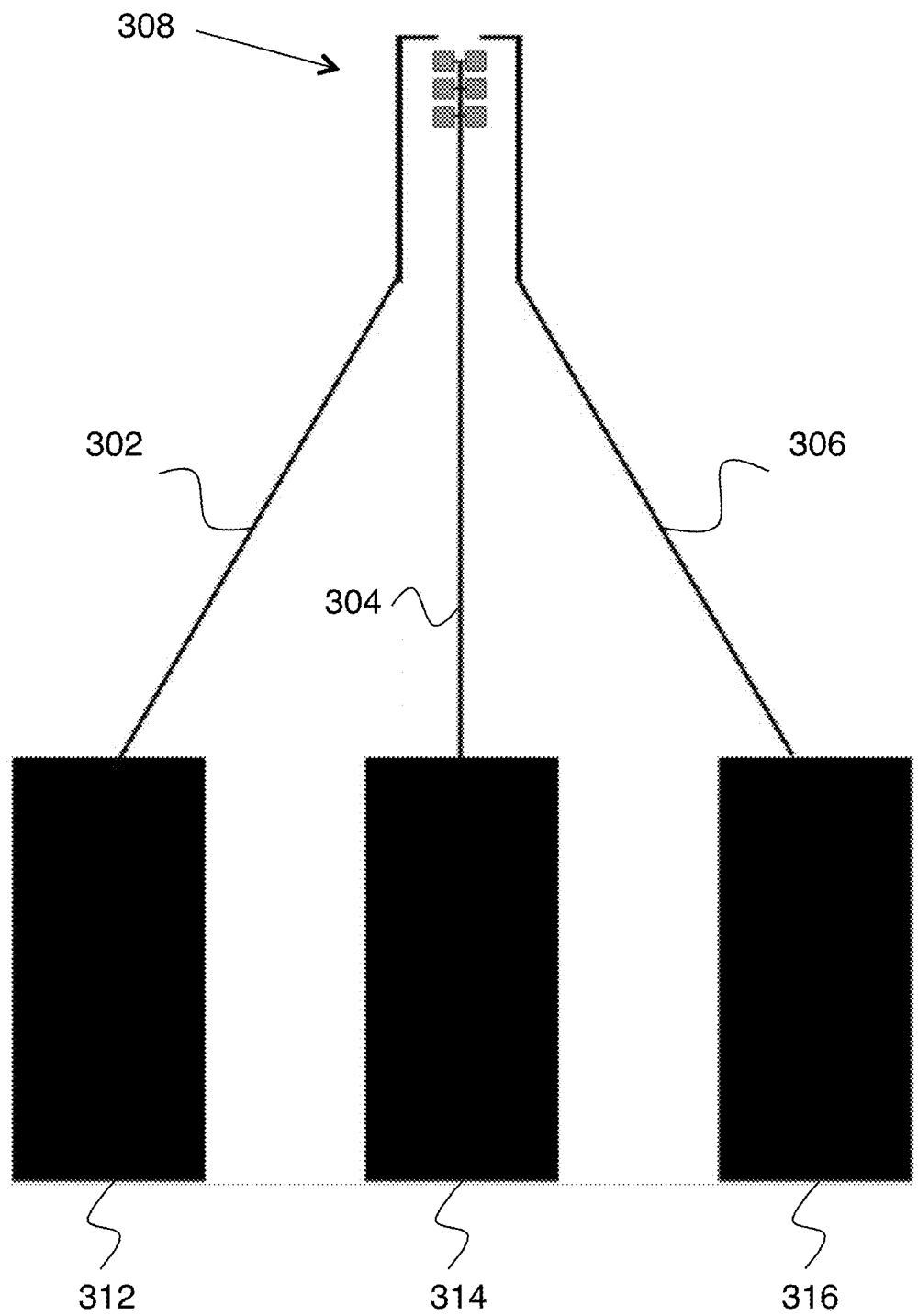
FIG. 3 shows further details of a preferred electrode configuration for performing an electrochemical impedance assay according to an embodiment of the invention.
Figure 4:
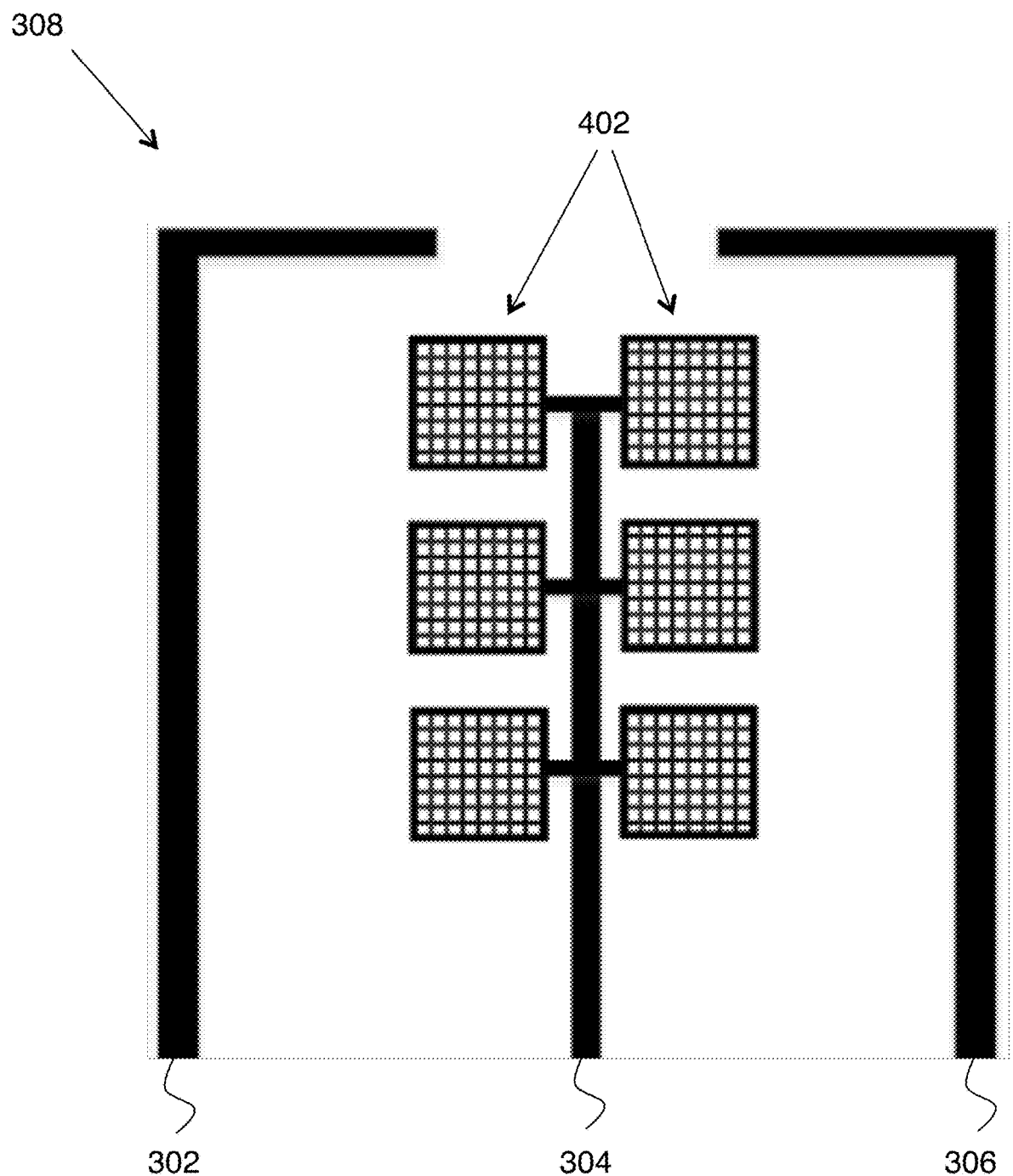
FIG. 4 is an enlarged view of part of the example of FIG. 3.
Figure 5:
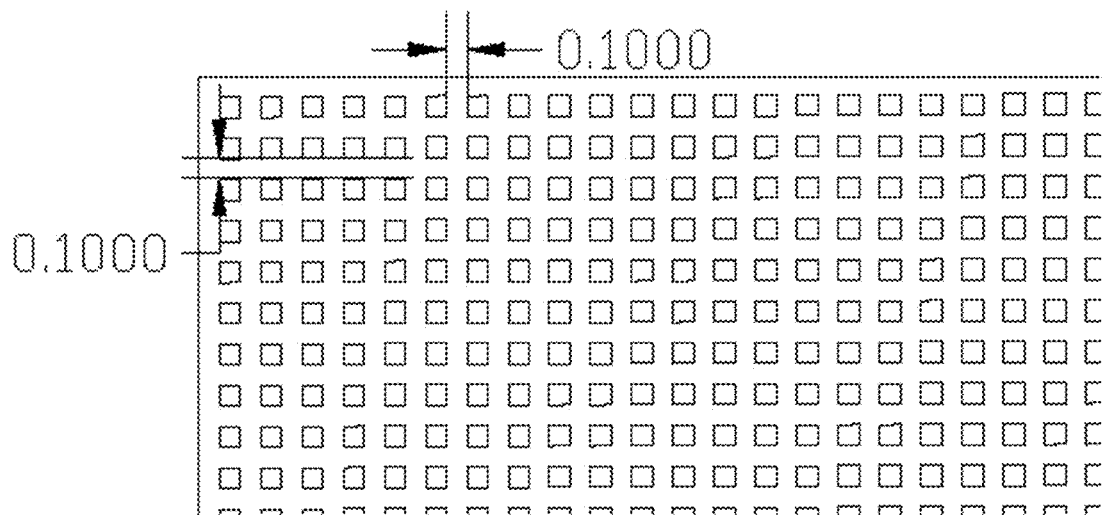
FIG. 5 shows further details relating to the example of FIGS. 3 and 4.
Figure 6:
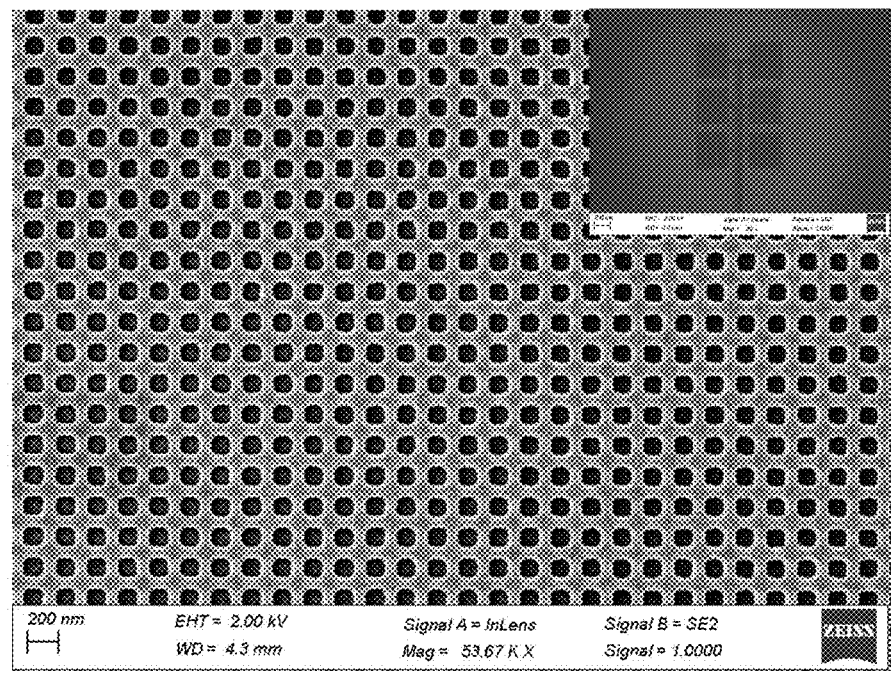
FIG. 6 is a scanning electron microscope image of an e-beam resist pattern for the nanogrid electrode of the example of FIGS. 3 and 4.

FIG. 3 shows further details of a preferred electrode configuration. Here 302 is a platinum counter electrode, 304 is the nanogrid working electrode and 306 is a Ag/AgCl reference electrode. 312, 314 and 316 are contact pads for electrodes 302, 304, and 306 respectively. FIG. 4 shows an enlarged view of region 308 on FIG. 3. Here the nanogrids 402 are more apparent, and each of these nanogrids 402 would have metallic nanoparticles on them as on FIG. 2. FIG. 5 shows an exemplary nanogrid design having 100 nm line widths and 100 nm square apertures. The squares seen in the figure will be spaces in the nanogrid after this pattern is made in a chromium mask. FIG. 6 is a scanning electron microscope image of an e-beam resist pattern for this nanogrid pattern.

Fabrication:

The fabrication of the nanogrid in FIGS. 3-5 can be done by microfabrication methodologies such as photolithography, physical vapor deposition, wet etching, dry etching and other techniques such as electrodeposition and soft lithography. The dimension of the grid spacing and lines are preferably designed to be 100 nm as shown in FIG. 5. With the electrodeposition of the gold nanoparticle and antibody conjugates, the spacing is expected to reduce since the conjugate will deposit on top of the grid and the exposed side walls of the metal grid. This will give more surface area and more sensitivity.

Figure 7A:
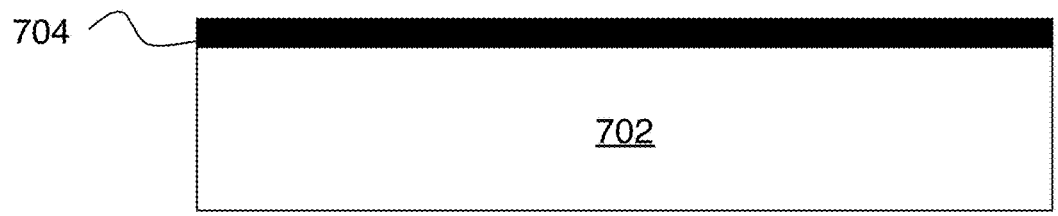
FIGS. 7A-F show an exemplary fabrication sequence for a nanogrid electrode.
Figure 7B:
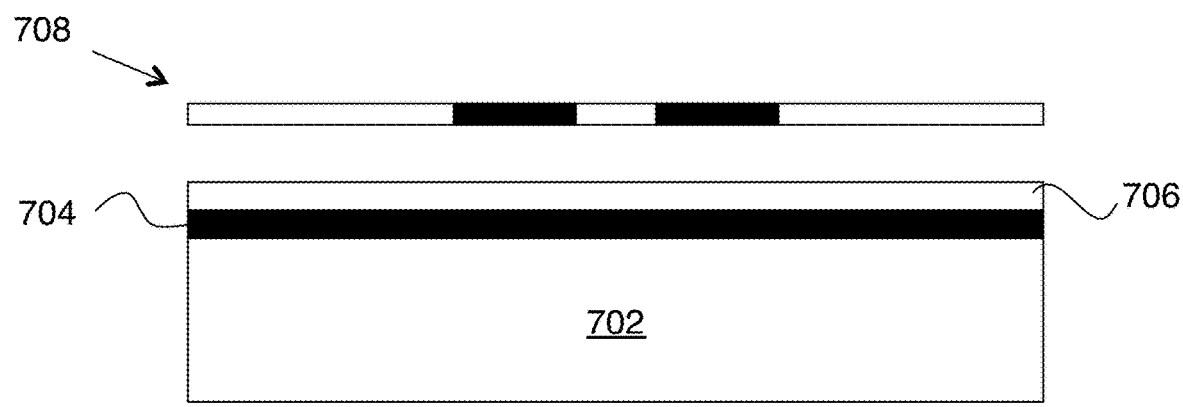
Figure 7C:
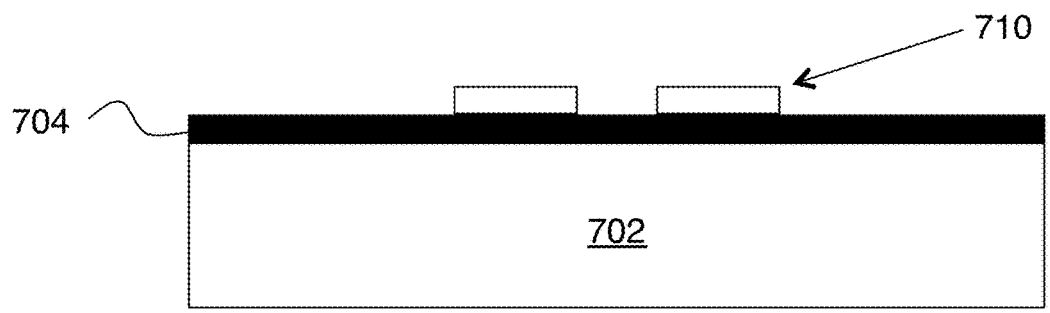

FIGS. 7A-F show an exemplary fabrication sequence for a nanogrid electrode. FIG. 7A shows an initial configuration with electrode metal 704 (e.g., Pt/Ti) disposed on a substrate 702 (e.g., quartz). FIG. 7B shows a photoresist layer 706 disposed on the structure of FIG. 7A, and a mask 708. FIG. 7C shows the result of patterning photoresist layer 706 to provide electrode resist pattern 710. It should be noted that this electrode resist pattern will define the overall shape of the electrodes (e.g., as shown on FIG. 3), but does not define the apertures for the nanogrid.

Figure 7D:
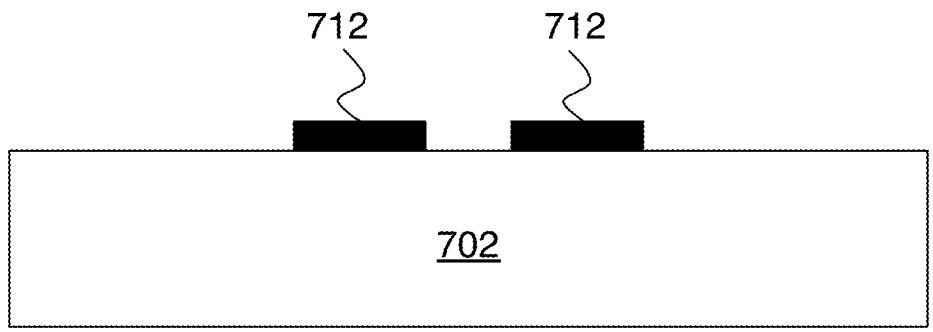
Figure 7E:
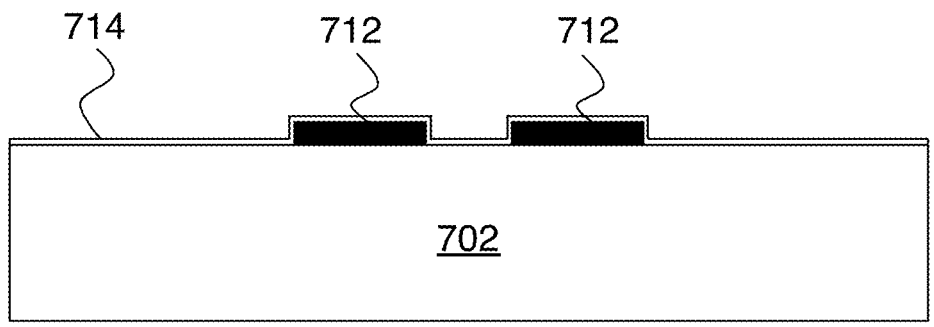
Figure 7F:
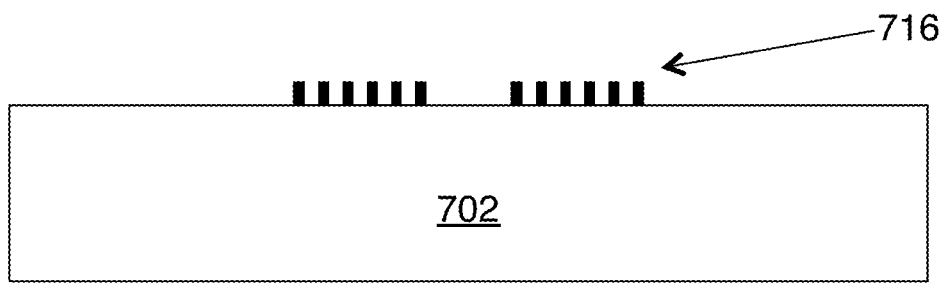

FIG. 7D shows the result of transferring resist pattern 710 to electrode metal 704 to provide an electrode pattern 712, e.g., by wet chemical etching. FIG. 7E shows the result of depositing e-beam resist 714 on the structure of FIG. 7D. FIG. 7F show the result of patterning e-beam resist 714, followed by ion milling to define the apertures in the nanogrid electrode, followed by removal of e-beam resist 714. The resulting electrode structure includes nanogrids 716 (e.g., as shown on 402 of FIG. 4).

The invention claimed is:

1. A method of performing electrochemical impedance spectroscopy for detection of chemical species, the method comprising:
   providing a working electrode for electrochemical impedance spectroscopy;
   bonding metallic nanoparticles to the working electrode with an electrodeposition process;
   conjugating the metallic nanoparticles with at least one first receptor species;
   detecting at least one first target species according to impedance changes at the working electrode caused by binding of the first target species to the first receptor species;
   wherein the conjugating the metallic nanoparticles with at least one receptor species is performed prior to the bonding metallic nanoparticles to the working electrode with an electrodeposition process.

2. The method of claim 1, further comprising conjugating the metallic nanoparticles with alkyl chains between 14 to 18 hydrocarbons for adsorption of serum albumin.

3. The method of claim 1, wherein the working electrode is configured as a grid having sub-micron apertures.

4. The method of claim 3, wherein the grid includes two or more row lines, wherein the grid includes two or more column lines, and wherein the row lines are perpendicular to the column lines.

* * * * *